United States Patent [19]
Volkmann

[11] Patent Number: 5,431,056
[45] Date of Patent: Jul. 11, 1995

[54] METHOD FOR DEPTH COMPENSATION OF AMPLITUDES OF ECHO-SIGNALS IN AN ULTRASONIC MEASURING DEVICE WHICH USES THE PULSE-ECHO-TECHNIQUE

[76] Inventor: Klaus Volkmann, Feldstr. 121a, D-5060 Bergisch-Gladbach, Germany

[21] Appl. No.: 136,536

[22] Filed: Oct. 14, 1993

[30] Foreign Application Priority Data

Oct. 15, 1992 [DE] Germany ............... 42 34 860.9

[51] Int. Cl.$^6$ ........................................ G01N 29/04
[52] U.S. Cl. .............................. 73/631; 73/602; 73/597
[58] Field of Search ................ 73/631, 602, 607, 597, 73/577

[56] References Cited

U.S. PATENT DOCUMENTS

| | | | |
|---|---|---|---|
| 4,102,205 | 7/1978 | Pies et al. | 73/614 |
| 4,398,423 | 8/1983 | Takahashi | 73/631 |
| 4,513,621 | 4/1985 | Renzel et al. | 73/631 |
| 4,545,251 | 10/1985 | Uchida et al. | 73/631 |

Primary Examiner—Hezron E. Williams
Assistant Examiner—Helen C. Kwok
Attorney, Agent, or Firm—K. S. Cornaby

[57] ABSTRACT

A method and apparatus for depth compensating the amplitudes of echo signals in an ultrasonic measuring device to compensate for virtually unlimited depth measurements using an amplifier adjustment curve supplied in real time which is triggered with every radiated pulse, and using the time-synchronous clock steps of a clock pulse generator converted to an analogue output signal through a D/A-converter.

8 Claims, 1 Drawing Sheet

METHOD FOR DEPTH COMPENSATION OF AMPLITUDES OF ECHO-SIGNALS IN AN ULTRASONIC MEASURING DEVICE WHICH USES THE PULSE-ECHO-TECHNIQUE

BACKGROUND OF THE INVENTION

The invention relates to a method for depth compensation of amplitudes of echo-signals in an ultrasonic measuring device which uses the pulse-echo-technique, in the course of which as a first step ultrasonic pulses are sent from the probe of said ultrasonic measuring device into a trial object containing several, as far as possible identical, flaws in known distances from the surface and lined up in depth reflecting the pulses, such that they return into the same or another probe of the ultrasonic measuring device, where they arrive in a temporal order corresponding to the spatial order in depth and give rise to electrical signals with different amplitudes at the output of the receiver unit of the ultrasonic measuring device, the electrical signals being available as so-called nodes of interpolation with their amplitude and time values, and a digital correction signal being obtained from the deviation of the signal amplitudes at every single node of interpolation from a corresponding reference amplitude, the correction signal being stored and used, after conversion to an analogue correction signal, to control an adjustable amplifier, so that in a subsequent measurement of the same material flaws of the same kind will yield equally high amplitudes of echo signals irrespective of depth.

In high-quality ultrasonic devices, particularly in ultrasonic devices intended for nondestructive testing of materials, a depth compensation function is provided to compensate for the dependence of echo amplitudes on depth. In the method previously known from DE 26 23 522 C2, the material to be tested is divided into digital depth intervals, and for every digital depth interval a corresponding digital signal correction value is calculated. These signal correction values are stored. During the measurement proper the signal correction values are converted into analogue values which are used to correct the values of the ultrasonic signal received. A method with analogue storage of the correction values is known from U.S. Pat. No. 3,033,029.

The method described in DE 26 23 522 C2 which is representative for its class is disadvantageous in its necessity to store one amplitude value for each depth interval, and hence for each time increment. This leads to high storage requirements. The required storage size is calculated as the ratio of the depth range and the measure in depth of one depth interval. The potential penetration depth range is predetermined by the storage size. Finally, it is disadvantageous that the nodes of interpolation must be fitted into the given grid of depth intervals, and preferably nodes of interpolation must be equidistant.

SUMMARY OF THE INVENTION

At this point the invention comes into its own. It has the object of improving the method mentioned at the outset with the result that the maximum depth of a depth range to be corrected for is practically unlimited, that a smaller storage size is required, and that high resolution and linear interpolation between non-equidistant nodes of interpolation is possible. This object is achieved by a method of the type mentioned at the outset, further characterized in that the amplifier adjustment curve is supplied in real time, triggered with every radiated pulse, the adjustment curve being generated digitally in time-synchronous clock steps of a clock pulse generator and convened to an analogue output signal through a D/A-converter by storing the digital value of the amplitude of an initial value in a adder register and storing the digital value of the difference between the amplitudes of the first node of interpolation and the initial value respectively, divided by the number of intervening clock signals in a second register as a so-called first increment, by incrementing with each clock cycle the value of the adder register by the increment until, after reaching time value t, of the first node of interpolation, the first register holds the digital value of the first node of interpolation; then the second increment, that is the digital value of the difference in amplitudes between the second node of interpolation and the first node of interpolation, divided by the number of intervening clock signals is loaded from a memory to the second register, and the procedure is continued in the same way, until the last node of interpolation has been reached. The adjustment curve is thus supplied as an open polygon shaped like a staircase.

This method has a number of advantages: an arbitrarily high resolution of the stairstep function can be obtained without additional storage requirements. In the language of the closest prior art, the measure in depth of the digital depth intervals can be chosen arbitrarily small. Further, the nodes of interpolation need not be fitted into the relatively coarse grid of the depth intervals, where they could come to lie e.g. in the beginning, the middle or the end of a depth interval, but advantageously the nodes of interpolation themselves are used as initial and final values for the division into depth intervals, i.e., time increments. This means that the time increment between a node of interpolation and the subsequent node of interpolation is in general different from the time increment between the subsequent node of interpolation and the one which follows in turn. Nevertheless, in accordance with the invention, the process may be operated at a constant clock frequency as well, thereby making the storage of individual time increments for the respective intervals between two nodes of interpolation unnecessary, if a relatively high clock frequency is chosen, because in this case the fortuitous position of the node of interpolation within the depth interval causes smaller errors than with the state of the art technology. In both cases the correction curve is more exact than according to the known state of the art. Furthermore, with relatively few nodes of interpolation, even strongly arcuate curves may be approximated with small deviations. Finally, the low storage requirement is beneficial: it results in a great number of correction curves being storable in a memory which previously could hold but one correction curve according to the state of the art. Besides, the measure in depth is unlimited, since not the depth intervals and their maximum number are predetermined, but rather the nodes of interpolation themselves form the basis of the procedure. During storage it is sufficient to store the digital amplitude values of the nodes of interpolation and their time values. It is also possible, instead of the latter, to store the increments in time and amplitude respectively, which are to be valid between two nodes of interpolation for all intervals, even though it is possible to include calculating this increment each time, and read it into the second register at suitable times, while the increments for the preceding interval between two nodes of interpolation are still being used.

The initial value is adjustable. Advantageously it is likewise stored in a suitable memory. In particular, the memory of a microprocessor provided in the ultrasonic measuring device and controlling its function, or an additionally provided memory can be considered for this purpose.

THE DRAWING

Further advantages and features of the method are revealed in the remaining claims and the following description of an embodiment not to be interpreted as restrictive, which is explained with reference to the drawings, in which:

FIG. 1 is a schematic drawing in the form of a block diagram of a circuit for the depth compensation method according to the invention; and FIG. 2 is the diagram of a compensation curve, where the adjustment voltage $U_{st}$ is plotted against real time t.

DETAILED DESCRIPTION OF THE DRAWING

Figure 1:
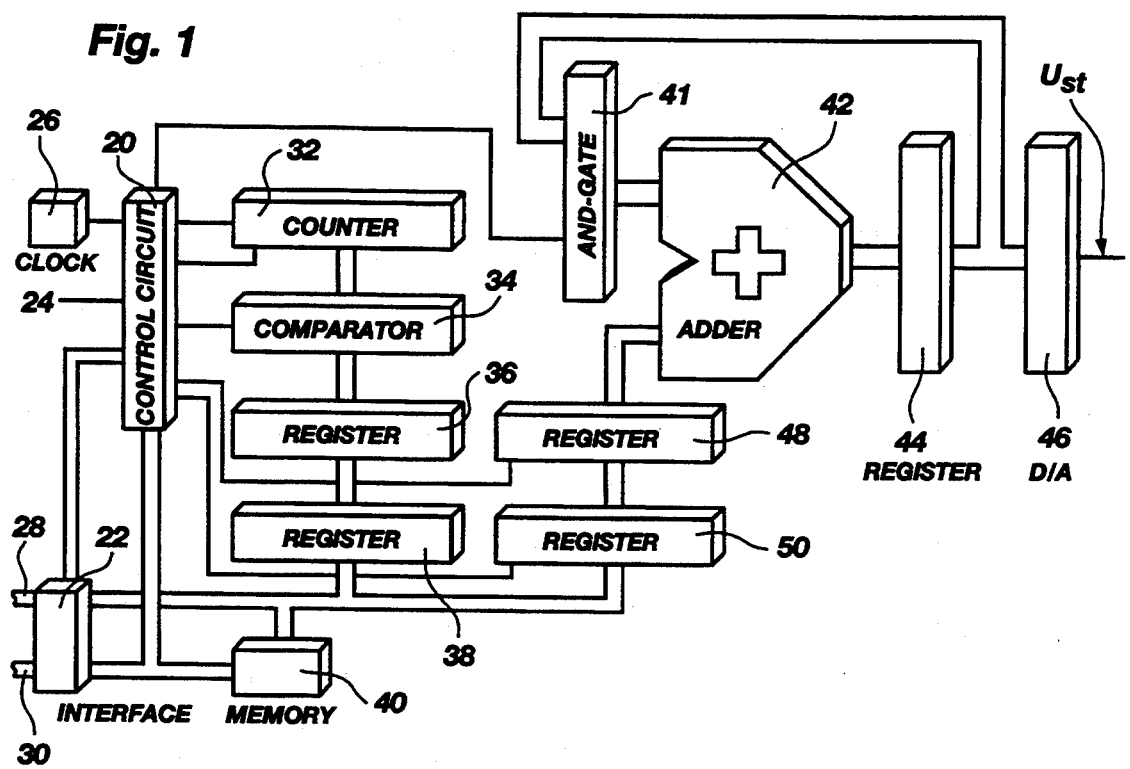

At its input side the depicted circuit is connected to the remainder of the electronic circuitry of an ultrasonic measuring device (not described in more detail here) on the one hand via a logical control circuit 20 provided as gate and on the other hand via an interface 22. Via an input 24 the logical control circuit 20 receives the so-called transmitter trigger pulse TTP, that is the signal directed at the pulse transmitter unit of the ultrasonic measuring device, causing it to release an acoustic pulse. The circuit according to FIG. 1 is started by the transmitter trigger pulse. A clock pulse generator 26 is furthermore assigned to the logical control circuit 20, its clock pulses are drawn upon by the circuit according to FIG. 1. In the embodiment shown it has a fixed frequency of 15 MHz. In another embodiment it has an adjustable frequency, which is readjusted for every interval between two nodes of interpolation.

The interface 22 is connected to a microprocessor (not shown) of the ultrasonic measuring device via a data line 28 on the one hand, and an address line 30 on the other hand.

A synchronous counter 32 started by the transmitter trigger pulse counts the clock pulses received from the clock pulse generator 26. At its output terminal the counter is connected to a comparator 34, to the second input of which there is connected the output of a register 36. In this register the number m of clock signals between two nodes of interpolation is stored. The number of clock signals for the interval between the two subsequent nodes is stored in a register 38 assigned to register 36; via a data line, register 38 in turn is connected to the interface 22 and a memory 40. This memory or the memory of the computer holds the values of the numbers of clock pulses for all intervals between the nodes of interpolation. Each time when the comparator 34 indicates that the number of clock cycles counted by the synchronous counter 32 is equal to the number of clock cycles previously stored in register 36, that is to say when the interval between two nodes of interpolation has been exhaustively processed, the new value m for the number of clock cycles is loaded to register 36 from register 38. In this way the subassembly for the generation of the control voltage $U_{st}$ of an adjustable amplifier is controlled, as will be set forth below.

An adder 42 forms pan of this subassembly. Its output terminal is connected to a register 44, the output of which is connected to a (first) input of the adder 42 via an AND-gate 41 on the one hand and with a digital-analogue-converter 46 on the other hand. The other (second) input of the adder 42 is connected to the output of a register 48, in which the voltage increment dU, valid for the current interval, is stored. Like register 36, register 48, too, has an associated register 50, holding at each time the voltage increment for the subsequent interval between two nodes of interpolation.

Now the procedure is as follows. Before the beginning of the generation of an adjustment curve, register 44 holds the digital value of the initial value $U_0$. Due to the feedback to the first input of the adder 42, this value is also available at the input of the adder 42. Further, the initial value $U_0$ is available at the input of the D/A-converter 46. It gives rise to an analogue output signal with the value $U_0$. When a transmitter trigger pulse arrives, with the first clock cycle the adder 42 adds the value of the voltage increment $dU_0$ (digital) and stores the result $U_0 + dU_0$ in the register 44; from there it is, on the one hand, convened to an analogue output signal $U_0 + dU_0$ in the D/A-converter 46; on the other hand it is available at the first input of the adder 42. With the second clock cycle the increment $dU_0$ is once again added to the initial value $U_0$ already increased by the $dU_0$, such that the analogue voltage $U_0 + 2dU_0$ is available at the output of the D/A-converter 46. This procedure is continued through so many clock cycles, until the number of clock cycles $m_0$ preset in register 36 has been reached. At this point the value of the output voltage amounts to $U_0 + m_0 dU_0 = U_1$. Now not only the content of register 38, that is the number $m_1$ of clock cycles for the subsequent interval, is loaded into register 36 but also the value of the voltage increment $dU_1$, valid for the next interval, is loaded from register 50 into register 48. The increment may be positive or negative. The process then proceeds for the new interval as described above, until this one, too, has been exhaustively processed and thus the second node of interpolation has been reached. When reaching the last node of interpolation the generation of the adjustment curve has been completed.

The described method is suited for an improved approximation of the polygonal adjustment curve. To this end, further nodes of interpolation are determined by calculation in addition to the measured nodes. For this the computer of the ultrasonic measuring device selects additional (calculated) nodes according to a preselectable algorithm. For example, the adjustment curve, represented until now as an open polygon between the nodes of interpolation, is approximated by arcuate curve sections, for example by cubic parabola segments for which a possible algorithm is the Akino-algorithm. In the place where the arcuate curve has a maximum deviation from the open polygon, a new node of interpolation is computed and inserted. Consequently, the open polygon approximates the arcuate curve in a better way than before. This process may be repeated as often as desired.

In a modified version of the circuit the synchronous counter 32 may be omitted. Instead its associated input of the comparator 34 is connected to the output of register 44. In this case, however, the register 36 must not hold the number of clock cycles, but rather the digital value of the terminating node of interpolation of the interval being processed, e.g. $U_1$ for the first interval between $U_0$ and $U_1$. When, after stepwise increase (or decrease) the same digital value is available at the output of register 44 as the one of the terminating node of interpolation of the interval ($U_1$ in the example), the terminating node of the subsequent interval ($U_2$ in the example) is loaded from register 38 to register 36; and simultaneously register 48 receives the new voltage increment ($dU_1$ in the example) for the subsequent interval (the second in the example) from register 50.

In another alternative, the clock frequency of the clock pulse generator 26 is additionally controlled, keeping the clock frequency fixed within each interval bounded by two nodes of interpolation.

The initial value $U_0$ is included in the concept of node of interpolation. Thus the first interval extends between the initial value $U_0$ and the first node of interpolation $U_1$.

Figure 2:
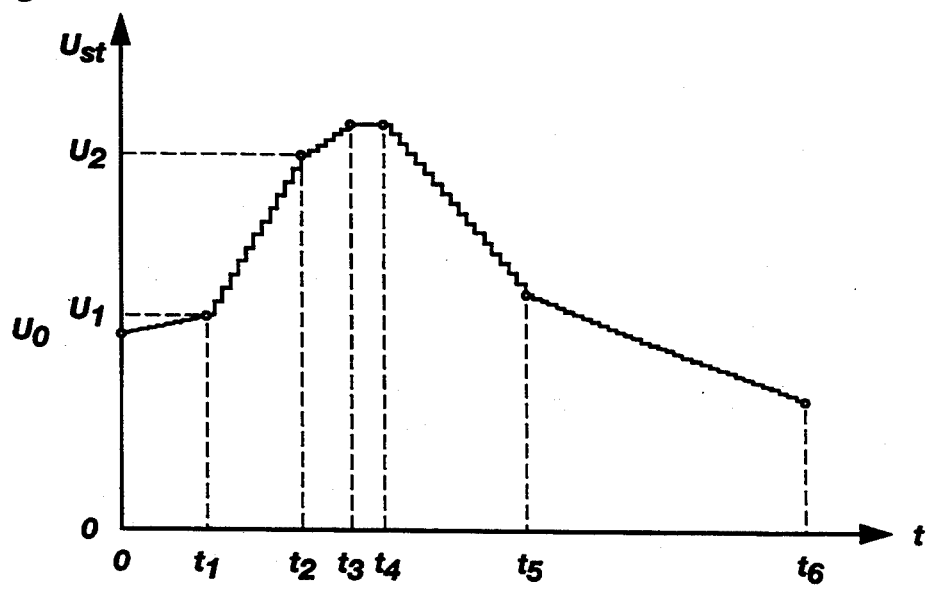

FIG. 2 shows the dependency of the voltage value $U_{st}$ of the compensation curve on time t. Starting with the analogue output value $U_0$, the output value is increased stepwise by $dU_0$, until the value $U_1$ of the first node of interpolation has been reached, after ten clock cycles, for $m_0=10$, have elapsed.

In the second interval the value $U_1$ in turn is increased stepwise by a new increment $dU_1$, until the value $U_2$ of the second node of interpolation has been reached after $m_1$ clock cycles. This is continued up to the sixth node of interpolation $U_6$. The compensation curve also displays negative increments, namely $dU_4$ and $dU_5$, and the voltage increment zero for $dU_3$.

In the practical implementation the units 32 to 38 and 42, 44, 48 and 50 have been designed in 16-bit technology; as an exception the D/A-converter 46 can only process 12 bits. The upper 12 bits are used for conversion, the lower four bits are rounded. Rounding-off errors are so small, that the cost savings achieved by using a twelve bit D/A-converter have no noticeable technical consequences for the practical compensation curve.

In another advantageous procedure, the clock pulse generator 26 has a fixed frequency of, for example 15 MHz. The synchronous counter 32 continuously counts the clock cycles starting with the initial value $U_0$ and finishing with the last node of interpolation $U_n$, thus the counting operation is not started anew with each interval. At each time register 36 contains (as described above) the number of clock signals attributed to the next node of interpolation, counted from the initial value $U_0$; for instance in the case of the third node of interpolation this is the numerical value $m_0+m_1+m_2$. In this way the counter 32 does not need to be reset at every node of interpolation.

The nodes of interpolation for several compensation curves are stored in the memory 40, designed as RAM and having a capacity of two KByte in one embodiment. The curve required at any one time is selected beforehand by suitable measures. Its data are then immediately available from the RAM; within few clock cycles, for example three clock cycles, they can be loaded from the memory 40 to register 36 and register 48 via their respective preregisters 38 and 50. In this way the microprocessor of the ultrasonic measuring devices does not itself take part in the generation of the compensation curve. It is, however, drawn upon for the mathematical computation of curves, the approximation of curves, etc., that is for processes not requiring real time processing. Since the essential data are stored in the memory 40, they can be rapidly accessed, enabling even the processing of nodes of interpolation in short succession and of high repetition rates of sound release, for example 10 kHz. Basically the microprocessor should take care of all processes not running in real time, whereas all data required in real time should be held in the memory 40.

I claim:

1. A method for depth compensation of amplitudes of echo-signals in an ultrasonic measuring device which uses the pulse-echo-technique, in the course of which ultrasonic pulses are sent from a probe of said ultrasonic measuring device, which said probe is acoustically coupled to a surface of a trial object, into said trial object containing several, as far as possible identical, flaws in known distances from said surface and arranged in different depths reflecting the pulses, such that the pulses return into the probe or into another probe of the ultrasonic measuring device, which said other probe is acoustically coupled to said surface, where the pulses arrive in a temporal order corresponding to the spatial order in depth and give rise to electrical signals with different amplitudes at an output of a receiver unit of the ultrasonic measuring device, the electrical signals being available as nodes of interpolation where each of said electrical signals having an amplitude and a time value, and a digital correction signal being obtained from the difference of the amplitudes of every said nodes of interpolation and a corresponding reference amplitude, the correction signal being stored and used, after conversion to an analogue correction signal, to control an adjustable amplifier, so that in a subsequent measurement of material of the same kind as the flaws in the trial object will yield equally high amplitudes of echo signals irrespective of depth, characterized in that an amplifier adjustment curve is supplied in real time, triggered with every said ultrasonic pulses, the adjustment curve being generated digitally in time-synchronous clock steps of a clock pulse generator and converted to an analogue output signal through an A/D-converter by storing the digital value of the difference $U_1-U_0$ between the amplitudes $U_1$ of a first node of interpolation and an initial value $U_0$ respectively, divided by a number $m_0$ of intervening clock signals in a first register as a first voltage increment $dU_0$, by incrementing with each clock signals a value contained in an adder register by the increment $dU_0$ until, after the amplitudes $U_1$ is of the first node of interpolation has been reached after the number $m_0$ of clock signals, the digital value of the first node of interpolation is available at the adder register, then a second voltage increment $dU_1$, that is the digital value of the difference $U_2-U_1$ between the amplitudes of a second node of interpolation and the first node of interpolation, divided by the number $m_1$ of intervening clock signals is loaded from a memory to the first register, and the method is continued in the same way, until the last of said node of interpolation has been reached.

2. A method according to claim 1, further characterized in that the initial value $U_0$, the increments $dU_n$ for the intervals between the nodes of interpolation including the sign of said increments, and the number of clock signals $m_0+m_1...+m_n$ are stored each time.

3. A method according to claim 1 further characterized in that the initial value $U_0$, the increments $dU_n$ for the intervals between the nodes of interpolation $U_1, U_2, ... U_n$ are stored.

4. A method according to claim 2 further characterized in that in addition a time increment dt is stored each time for each interval between two said clock signals.

5. An apparatus for compensating depth amplitudes of echo-signals in an ultrasonic measuring device, characterized in that ultrasonic pulses are sent from a probe of said ultrasonic measuring device such that said probe is acoustically coupled to a surface of a trial object, said pulses are returned to said probe in a temporal order corresponding to the spatial order in depth and give rise to electrical signals with different amplitudes at an output of a receiver unit of said ultrasonic measuring device, the electrical signals being available as nodes of interpolation, and digital correction signals being obtained from the difference of said amplitudes of said nodes of interpolation and a corresponding reference amplitude, a comparator having an input terminal which said comparator is connected at said input terminal on the one hand with a first register, in which a number of clock signals per interval is stored for a respective interval and on the other hand is connected with a synchronous counter for counting said clock signals, an adder register is provided, having an output terminal which is connected to a second register, the output of said second register being connected to a D/A-converter on the one hand, and an input of said adder register on the other hand and a second input of said adder register being connected to a third register, in which a voltage increment $dU_n$ is stored.

6. An apparatus according to claim 5 further characterized in that the clock signals are produced in a clock pulse generator which has an adjustable clock frequency.

7. An apparatus according to claim 5 further characterized in that said registers, said synchronous counter, said comparator, and the said adder register are designed in a 16-bit technology and that the D/A-converter is designed in a 12-bit technology, the lower four bits of the 16 bits being rounded off during the conversion to an analogue signal.

8. An apparatus according to claim 5 further characterized in that a memory is provided to store said digital correction signals, said voltage increment, and said number of clock signals.

* * * * *